United States Patent [19]

Linkow et al.

[11] Patent Number: 4,661,066
[45] Date of Patent: Apr. 28, 1987

[54] MOVABLE PLATE IMPLANT

[76] Inventors: Leonard I. Linkow, 1530 Palisades Ave., Fort Lee, N.J. 07024; Leo Hoffman, 15 Woodmere Blvd., Woodmere, N.Y. 11598

[21] Appl. No.: 801,639

[22] Filed: Nov. 25, 1985

[51] Int. Cl.⁴ .............................................. A61C 8/00
[52] U.S. Cl. ................................................... 433/176
[58] Field of Search ................................. 433/173–176

[56] References Cited

U.S. PATENT DOCUMENTS

| 622,670 | 4/1899 | Dwight | 433/221 |
| 4,062,119 | 12/1977 | Linkow et al. | 433/176 |
| 4,459,111 | 7/1984 | Valen | 433/176 |

FOREIGN PATENT DOCUMENTS 1062885 8/1959 Fed. Rep. of Germany ...... 433/220

Primary Examiner—Robert Peshock
Attorney, Agent, or Firm—Darby & Darby

[57] ABSTRACT

An oral implant for supporting an artificial tooth structure includes an implant portion that has a transverse slit at an obtuse angle to the side wall such that two facing surfaces are created. By squeezing the surfaces toward each other, the surfaces make contact and slide along each other so as to laterally separate the two parts of the implant portion. This causes the implant portion to become tightly wedged in a groove in a patient's bone along the occlusal plane. Additionally, the implant includes a neck portion with a rotatable threaded collar that couples to threads on a cap to which the artificial tooth structure is secured. As a result, the tooth structure can be removed without damage to it or to the implant.

30 Claims, 17 Drawing Figures

MOVABLE PLATE IMPLANT

BACKGROUND OF THE INVENTION

This invention relates to dental implants and, more particularly, to dental implants that are easily installed and adapted to be detachably connected to a bridge for artificial teeth.

Dental implants have become a rather standard technique for supporting an artifical tooth structure, e.g. artificial teeth or bridges, in edentulous spans. These implants typically include an implant portion or blade and a neck portion with a cap or post at its end. The blade is inserted directly into the patient's maxillary or mandibular bone where the artifical tooth is to be located. This is accomplished by making an incision in the alveolar tissue over the ridge crest and reflecting the tissue to expose the bone. A burr is then used to create a groove in the bone which is slightly less than the size of the blade. The blade is located in the groove and tapped lightly into the place, where it is held by friction.

Either immediately, or later when bone has regrown about the blade to secure it in place, the artificial tooth or a bridge support structure is fastened to the cap or post, e.g. by cement.

Great care must be taken by the dentist in forming the groove for the blade. Should the groove be too narrow, tapping the blade into place is likely to cause severe trauma to the bone, which may cause the bone to fracture, the implant to come loose and additional bone loss. If it is too wide, there is insufficient contact between the blade and groove, and the blade will not remain in place.

There are available in the prior art, devices that permit the installation of a blade in a groove which is to wide. Typical of these devices are those described in U.S. Pat. No. 3,683,501 of Edelman, U.S. Pat. No. 4,081,908 of Sneer and U.S. Pat. No. 4,521,192 of Linkow, one of the present inventors. However, even these devices require considerable skill by the oral surgeon for their use.

Even when the implant is successful, it may be necessary for a variety of reasons to remove an artificial bridge supported by the implant. The standard procedure in such a case is to cut the bridge into sections for removal. However, this procedure may unintentionally weaken the implant. Therefore it is desirable to provide a means for removing a bridge structure in one piece from an implant. Such an arrangement is shown in U.S. Pat. No. 4,531,917 of Leonard Linkow and Leo Hoffman, the present inventors. However, the method and apparatus of that patent require the use of small screws, which may be difficult to reach and manipulate.

SUMMARY OF THE INVENTION

The present invention is directed to providing an implant which can be inserted in the patient's bone adjacent the occlusal plane without significant risk of trauma. The invention is also directed to several means for detachably connecting a bridge or artificial tooth structure to the implant.

In an illustrative embodiment of the invention the blade has at least one laterally oblique slit in longitudinal cross section which is positioned toward one end and which extends from the top of the blade to a location near its bottom, or vice versa. Indentations, projections or other means are provided on both sides of the slit such that the portions of the blade on each side of the slit can be grasped by a tool and squeezed toward each other. Because the slit is oblique in lateral cross-section, the two portions of the blade slide past one another and move laterally with respect to each other. This causes the blade to become wedged securely in the groove, without the need to tap the blade in place with a mallet. Also the amount of lateral pressure on the walls of the groove created by the blade is directly and controllably related to the amount by which the blade portions are squeezed together.

The cap or post on which an artificial tooth or bridge support is mounted is provided with a hollow interior in which there are screw threads. These threads are engaged by corresponding screw threads that are located on a collar that is rotatably secured about the neck of the implant.

Various techniques are utilized for securing the collar to the neck. In one embodiment the neck has left-hand threads at its upper end that engage similar threads on the interior of the collar. The collar is then screwed onto the neck beyond the left-hand threads such that it is freely rotatable and is axially displacable only slightly. Right-hand threads on the outer surface of the collar and the interior of the cap can then be used to attach the cap to the rest of the implant.

In another embodiment the collar is held on the neck by a transverse pin.

A still further embodiment utilizes a collar with a transverse slit extending through the porton of the collar with threads. When the cap is screwed onto the collar, the threaded portions of the collar on either side of the slit are forced together, thereby gripping the neck of the implant.

An additional embodiment of the invention employs a cap with an externally threaded extension and an unthreaded cavity for receiving the neck. The threaded extension has a transverse slit through part of it. When a collar with internal threads is screwed onto the cap, the portions of the threaded extension on either side of the slit are forced together and grip the neck of the implant.

BRIEF DESCRIPTION OF THE DRAWINGS

The foregoing and other features of the present invention will be more readily apparent from the following detailed description and drawings of illustrative embodiments of the invention in which.

DESCRIPTION OF ILLUSTRATIVE EMBODIMENTS

Figure 1:
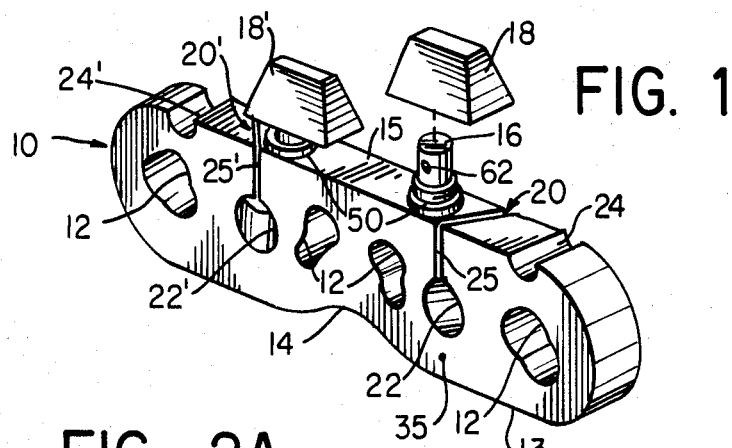
FIG. 1 is a perspective view of an implant blade, neck and cap according to a first embodiment of the present invention.

In FIG. 1 there is shown a greatly enlarged perspective view of an osseous implant according to the present invention. This implant is suitable for use in edentulous spans in the alveolar ridge crest of patients. The implant includes a blade portion 10 which is adapted to be located in the bone of the patient. Preferably this blade portion is formed from titanium. It includes holes or vents 12 which allow bone to grow through the blade and anchor it in place. In addition, the blade may have various configurations which make it suitable for insertion in the patient's bone. For instance, the blade of FIG. 1 has a raised portion 14 along its lower edge, as viewed in the drawing, in order to avoid the sinus cavity of a patient.

Extending upwardly, as viewed in FIG. 1, from the upper surface 15 of the blade portion 10, are neck portions 16. There may be one neck on a blade portion or more than one, as desired. Further, the neck portions may have a rectangular, circular or other configuration as desired. Attached to each neck portion 16 is a post or cap portion 18. This cap 18 is used to support an artificial bridge structure or an artificial tooth 11 as shown more clearly in FIG. 12.

Figure 2A:
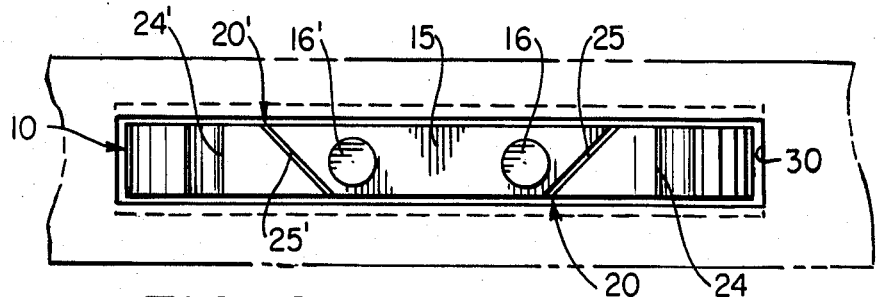
FIGS. 2a and 2b are top views of the blade in the initial insertion and wedged positions in the bone of a patient, respectively.
Figure 2B:
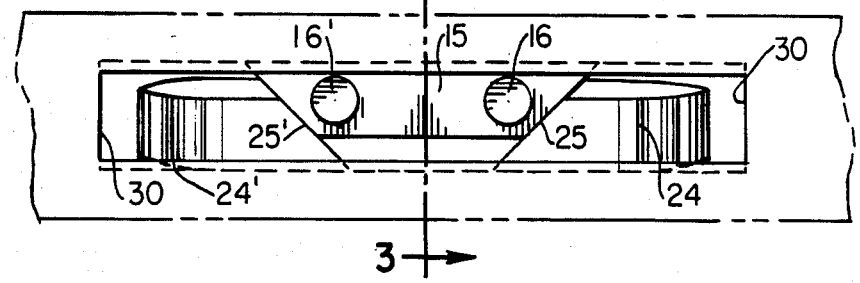

The blade portion 10 of the implant also includes at least one, and preferably two, laterally oblique slits 20, 20' as viewed from the top or in longitudinal cross section. These slits extend from the upper surface 15 of the blade to bending holes or openings 22, 22' near the bottom edge 13 of the blade. In addition, recesses 24, 24' are located in the upper surface 15 of the blade toward the outside of the slits 20, 20'. As best seen in FIGS. 2A and 2B the opposing surfaces 23 and 25 on either side of each slit are at an angle with respect to the side walls of the blade portion 10.

In utilizing the present invention, an incision is made in the fibromucosal tissue of the patient down to the underlying alveolar ridge crest bone. The tissue is then reflected to expose the bone and a burr is used to create a groove 30 in the bone which is shown in cross section in FIG. 3. This groove is at least as deep as the height of the implant blade 10. Preferably the burr is used to slightly undercut the bone such that undercut surfaces 32 are formed.

In conventional implant surgery the groove is made to have nearly the same width as the width of the blade, so that when the blade is inserted it will make frictional contact with the walls of the groove and will hold the blade in place. In order to accomplish this the groove is typically made slightly narrower at its bottom than at its top. Consequently, a mallet is used to tap the blade into place at its final depth, thus assuring that there is sufficient frictional contact between the blade and the groove in the bone. However, forming the groove and tapping the blade in place must be done with expert skill in order to avoid excessive trauma to the bone because of too narrow a groove or a loose implant because of too wide a groove.

Figure 3:
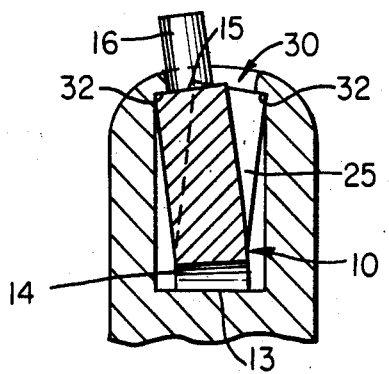
FIG. 3 is a cross-sectional view of the blade of FIG. 2b along lines 3—3.

In the present invention the groove is made sufficiently wide over its entire depth so that the blade can be manually inserted in place. Once in place a tool is utilized to squeeze together the portions of blade 10 on either side of slits 20, 20'. Where only one slit 20 is present this can be accomplished by a pair of pliars which engage the neck 16 adjacent the slit and the recess 24. As these two portions are brought together, surfaces 23 and 25 (FIG. 2a) come into contact with each other. Further squeezing together of the portions causes surfaces 23 and 25 to slide laterally along each other such that the portions of the blade on opposite sides of the slit move laterally with respect to each other and come into frictional contact with the walls of the groove (FIG. 2b).

Where both slits 20 and 20' are present, the recesses 24, 24' can be grasped with a tool and squeezed together. By squeezing these portions sufficiently, the ends of the blade move laterally with respect to the middle (FIG. 2b) and the frictional contact is such that the blade is securely locked in place in the groove. This is especially true if the grooves have been formed with undercut surfaces 32 as shown in FIG. 3. These surfaces 32 contact the upper surface 15 of the blade portion and trap the blade within the groove. Since the blade is made out of titanium material there is very little spring to the metal. Consequently, once it has been deformed into frictional contact with the groove, it will remain in that position.

Figure 4:
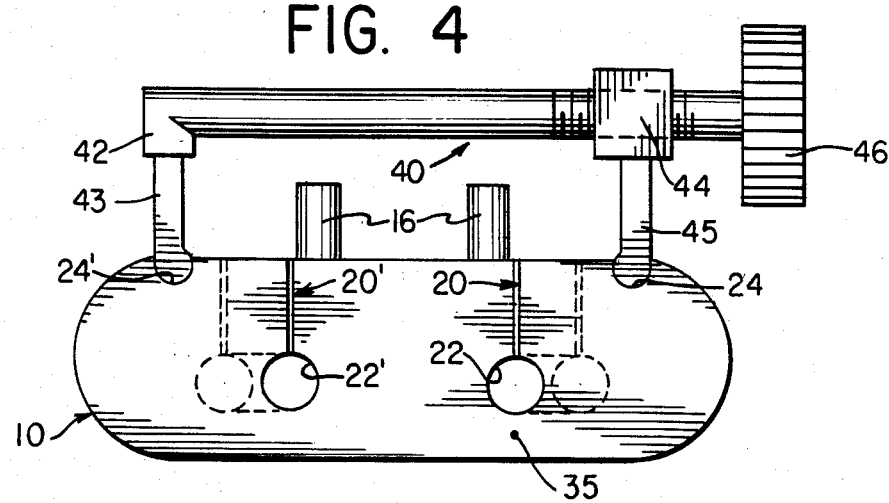
FIG. 4 is a side view of the implant of the present invention illustrating a tool for wedging the blade in a groove in the patient's bone.

Various means are provided for controlling the amount of lateral pressure that the blade applies to the groove. In particular, the size of the bending holes 22, 22' and the narrowness of the connecting portion 35 of the blade 10 between the holes 22, 22' and the bottom surface 13, control the amount of squeezing force necessary to achieve the lateral displacement of the blade portions. In effect, the narrower portion 35 is made, the easier it is to squeeze the two joined parts together. In addition, control of the squeezing action can be achieved through the use of an especially designed tool which has the general appearance of a screw caliper. This tool 40, as shown in FIG. 4, includes a threaded shaft 42 from which a leg 43 extends into contact with the recess 24'. A hollow portion 44 with internal threads receives the threaded shaft 42. Extending from the portion 44 is an additional leg 45 which is received in the recess 24 of the blade. By utilizing precision machine threads in the tool and a calibrated scale, particular rotations of the handle 46 at the end of shaft 42 will represent a particular displacement between the legs 43 and 45. By knowing the configuration of the slits 20, 20' of a particular implant blade, a particular amount of rotation of handle 46 can be directly related to a particular amount of lateral displacement of the joined blade parts as shown in FIG. 2b.

Since the prior techniques for inserting blades and the prior blades require great skill to avoid damage to the patient or failure of the implant, the technique was utilized only by specially trained dentists and oral surgeons. However, with the present invention, there is much less opportunity for harm and failure and, consequently, oral implants can be more widely utilized.

Figure 5:
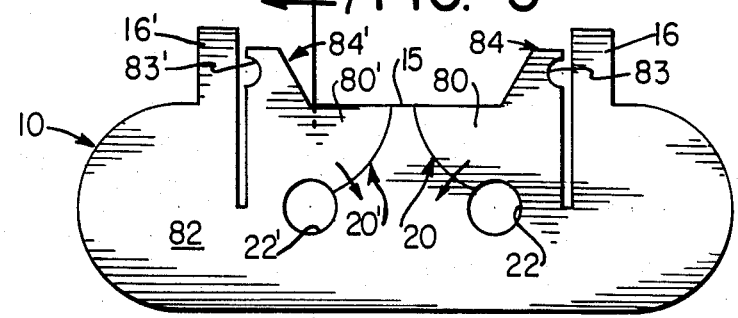
FIG. 5 is a side view of an implant according to the present invention in which an alternative structure for wedging the blade in a groove is shown.
Figure 6:
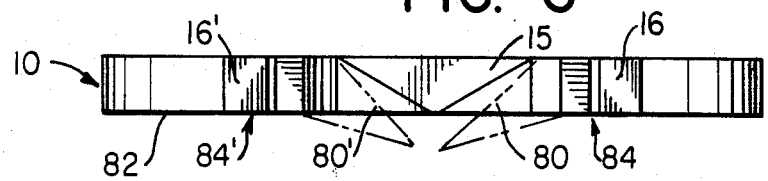
FIG. 6 is a top view of the implant of FIG. 5.
Figure 7:
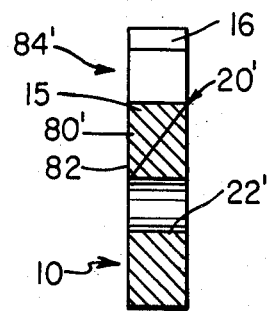
FIG. 7 is a cross-sectional view of the implant of FIG. 5 along lines 7—7.

In FIG. 5 there is shown a variation on the embodiment of FIG. 1. The blade 10 in FIG. 5 has oblique slits 20, 20' which lead to holes 22, 22' as in FIG. 1, but are arranged so as to form movable pieces 80, 80'. Pieces 80, 80' include a portion of upper surface 15 as best seen in FIG. 6, but taper toward the front side 82 of the blade 10 as viewed in FIG. 5. The taper is formed because the slit is at an oblique angle in lateral vertical cross section as best seen in FIG. 7.

Each piece has a respective projection 84, 84' which defines respective recesses 83, 83'. If a tool, e.g. pliers or tool 40, is used to contact recesses 83, 83' and squeeze them toward each other, parts 80, 80' tend to rotate downwardly as indicated by the arrows in FIG. 5. Because of the oblique and tapered shape of the pieces as defined by slits 20, 20', the pieces move laterally with respect to the rest of the blade as shown in dotted line in FIG. 6. This lateral movement wedges the blade in a groove in the patient's bone.

Figure 8:
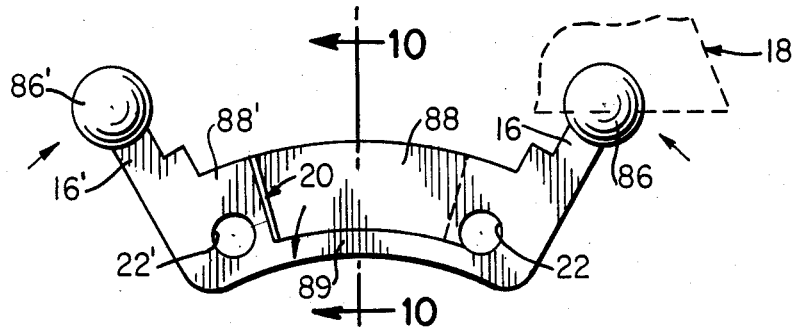
FIG. 8 is a side view of another alternative structure for wedging the blade in a groove and having spherical posts.
Figure 9:
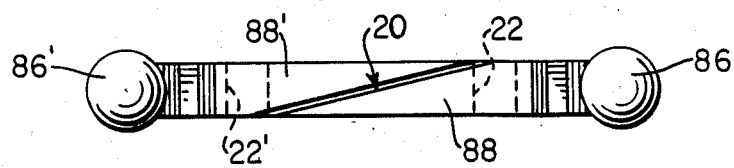
FIG. 9 is a top view of the implant of FIG. 8.
Figure 10:
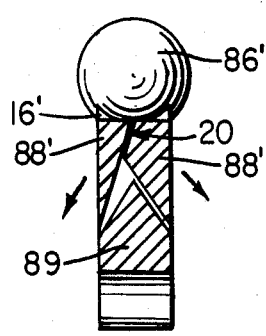
FIG. 10 is a cross-sectional view of the implant of FIG. 8 along lines 10—10.

Another variation on the embodiment of FIG. 1 is shown in FIGS. 8-10. In this embodiment the blade is divided into two parts 88, 88' by slit 20, which parts are joined along the bottom of the blade by a portion 89. At the ends of portion 89 are bending holes 22, 22'. As best seen in FIGS. 9 and 10 the slit 20 is laterally and vertically oblique.

The posts 16 for the blade of FIG. 8 extend outwardly at an angle and are topped by spherical surfaces 86. When this blade is positioned in the bone groove of a patient, a tool is used to squeeze the posts toward each other as shown by the arrows in FIG. 8. The posts 88, 88' move with respect to each other and the taper of their opposed surfaces and that of piece 89 cause them to move laterally away from each other and to wedge in the groove Also parts 88, 88' move downwardly with respect to part 89, thus causing posts 16 to assume a more upright position. Even if these posts 16 are not in a completely upright position when the blade is wedged in position, spherical surfaces 86 allow a cap to be applied to the posts in a vertical direction as shown in dotted line in FIG. 8.

Figure 11:
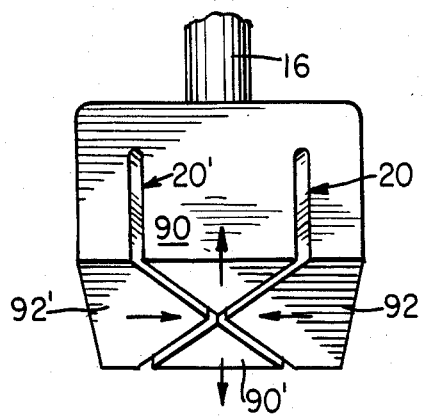
FIG. 11 is a still further alternative structure for wedging the blade in a groove.

FIG. 11 shows an embodiment wherein the slits 20, 20' extend from the bottom of the blade toward the top and criss-cross each other. As a result the blade is divided into connected parts 90, 90' and 92, 92'. If a tool is used to force parts 92, 92' toward each other, the criss-cross shape of the slits causes the parts 90, 90' to move away from each other as shown by the arrows. As a result, parts 90, 90' wedge against a groove in the patient's bone.

Regardless of the type of blade which is wedged in the patient's bone, the cap 18 may be cemented onto the neck 16 or formed integrally with it. Then the artificial tooth or support for the bridge can be cemented onto the cap 18. While there is little need to remove an artificial tooth once in place, it frequently becomes necessary to remove a bridge structure from the implant. In order to facilitate bridge removal without the destruction of the bridge or undue pressure on the implant, various techniques can be provided for attaching the cap to the neck.

In general, the techniques according to the present invention utilize a screw thread on the cap 18 which engages a threaded collar 50 that is located about the neck 16 (FIG. 1). This collar 50 is rotatable so that it can engage the threads of cap 18 and secure it in place with respect to the collar. However, means must also be provided for securing the collar to the neck before the implant is installed in a patient's mouth. One technique for accomplishing this is illustrated in FIG. 12.

Figure 12:
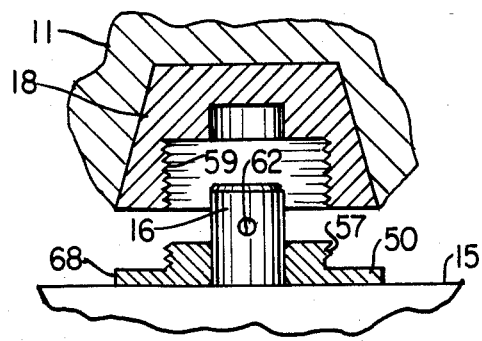
FIG. 12 is a partially sectioned side view of the attachment of the cap to the neck according to the embodiment of the invention shown in FIG. 1.

As shown in FIG. 12, the collar 50 may be retained on the neck 16 by a pin 62 which extends laterally through the neck at a sufficient distance above the collar to allow minimal axial displacement and rotation of collar 50. Peening or swedging the ends of the pin prior to inserting the implant in the patient's mouth, will keep the pin in place. After the implant is inserted in the patient's bone, the external threads 57 of the collar can then be screwed directly onto the internal threads 59 of the cap 18, such that the cap is connected to the implant.

Figure 13:
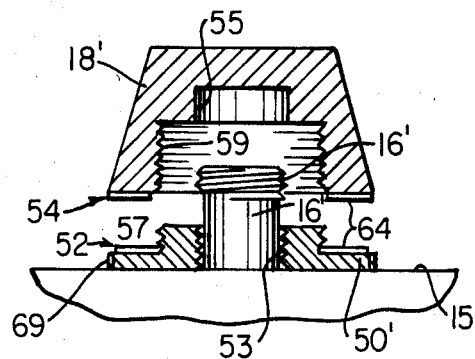
FIG. 13 is a partially sectioned side view of the attachment of the cap to the neck of the implant according to a second embodiment of the invention.

Another method of connecting the cap to the neck with a threaded collar is shown in FIG. 13. There the upper portion of the neck 16 includes a section of left-hand threads 16'. These threads may engage internal threads 53 on a collar 50'. Since the threads 16' are at a distance from the top surface 15 of the blade which is greater than the width of the collar, once the collar 50 has been screwed past threads 16', it is held on the neck with a minimal amount of permissible vertical displacement as viewed in FIG. 13; but, the collar 50' is freely rotatably.

Figure 16:
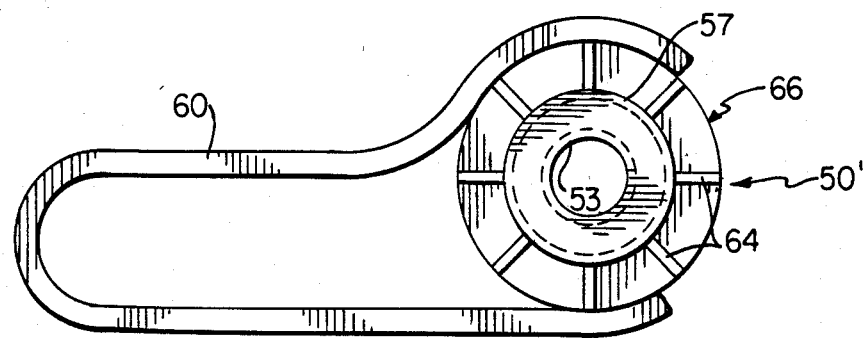
FIG. 16 illustrates a tool for connecting the cap to the neck of the implant by rotation of a collar.

The implant blade is next installed in the patient's bone. Attachment of the cap 18' to the neck 16 occurs either immediately after installation, or at a later time when bone has had a chance to grow through vents 12. This attachment is accomplished by lowering the cap over the neck 16 such that the threaded portion 16' extends into a recessed portion 55 of the cap and the exterior threads 57 of collar 50' engage the interior threads 59 of cap 18'. After collar 50' has been rotated a sufficient amount, the cap 18' is securely attached to the neck and the rest of the implant portion. To facilitate the rotation of collar 50, a tool, such as pinchers 60 shown in FIG. 16, may be utilized. In addition a pair of pliers with a fine point may be used for this purpose.

Projections 64 and/or recesses 66 may be located in the upper surface 52 of the collar 50' (FIGS. 13 and 16) and the lower surface 54 of the cap 18'. During the tightening process between these two parts, the projections and recesses will become locked together such that the collar 50' will not unscrew and loosen the connection. Near the end of this tightening process it will be necessary to force the respective projections on the two surfaces 52, 54 over each other such that the projections can be received in the recesses. However, the material is sufficiently pliable to allow this to be done.

Should it become necessary to remove the bridge from the implant, a tool, such as tool 60 or a pair of pliers, is used to unscrew collar 50'. Initially, enough force will have to be applied in order to deform the projections 64 sufficiently for the projections to ride out of the recesses in surfaces 52 and 54. However, after this has been accomplished, all that is necessary is the further unscrewing of collar 50' from cap 18'. During the unscrewing process it may be necessary to hold the bridge with pliers to prevent it from rotating as collar 50' is unscrewed.

Because of the size of cap 18 with respect to collar 50', the collar is generally hidden from sight by the artificial truth. The fibromucosal tissue of the patient may be sutured about collar 50' or, if sufficient vertical displacement is available, it may be located between the bottom of collar 50' and the upper surface 15 of the blade.

Figure 14:
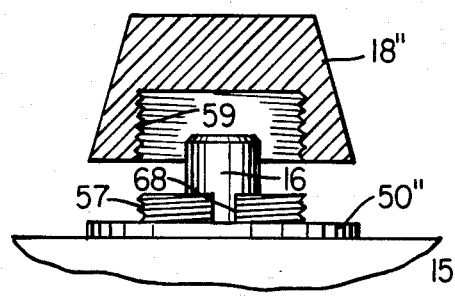
FIG. 14 is a partially sectioned side view of the attachment of the cap to the neck of the implant according to a third embodiment of the invention.

In a further alternative embodiment shown in FIG. 14, a collar 50" has a lateral slit 68 which extends across its diameter. The collar is located about neck 16, but is not otherwise held on neck 16. The diameter of the opening in cap 18" which contains the threads 59 is made such that screwing of collar 50" into cap 18" squeezes the portions on either side of the slit 68 together. This squeezes the collar onto neck 16, thus retaining it in place.

Figure 15:
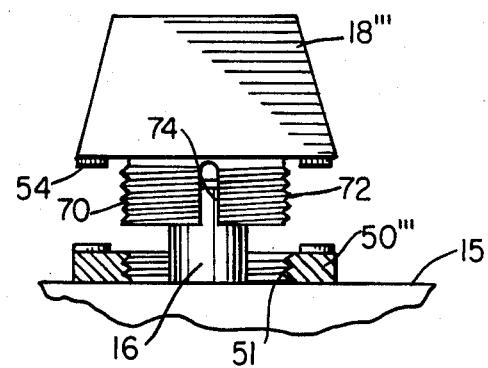
FIG. 15 is a partially sectioned side view of the attachment of the cap to the neck of the implant according to a fourth embodiment of the invention.

In a still further embodiment of the invention shown in FIG. 15, a cap 18''' is provided with a projecting portion 70 which contains external screw threads 72. In addition, the projecting portion 70 contains a transverse slit 74 extending across its diameter. A collar 50''' contains only internal threads 51 which engage the threads 72 of the cap 18'''. The threads 51 of the collar are arranged so that screwing of the collar 50''' onto the cap 18''' causes the portions of the cap projection 70 on either side of the slit 74 to squeeze together and lock the cap on neck 16.

The caps and collars illustrated in FIGS. 12, 14 and 15 may also contain the projections 64 and recesses 66 which are utilized in the embodiment of FIG. 13 to keep the collars from unscrewing, once in place. Further, in all of the embodiments shown, i.e. FIGS. 12–15, the outer surfaces 69 of the collars may be knurled or roughened to increase frictional contact between the collar and a pair of pliers or a tool, such as tool 60 shown in FIG. 16.

It is also possible to retain collar 50 on neck 16 by swedging or welding the end of the neck once the collar has been located on the neck. However, swedging is not strong enough with a material such as titanium, to assure permanent location of the collar on the neck. Further, welding will only allow attachment at one location. However, with the squeezing force generated by the embodiments of FIGS. 14 and 15, and the threaded connections in FIGS. 12 and 13, the attaching force is spread out along the neck area so that the titanium metal is not unduly stressed and deformed.

While the invention has a particularly shown and described with reference to preferred embodiments thereof, it will be understood by those skilled in the art that various changes in form and detail may be made therein without departing from the spirit and scope of the invention.

We claim:

1. An oral implant for supporting an artificial tooth structure comprising an implant portion adapted to be fitted in an exposed opening in a bone of a patient in the vicinity of the occlusal plane, said implant portion having two spaced-apart edge surfaces and two generally parallel and laterally spaced-apart side walls connecting said edge surfaces, said implant portion defining at least one slit extending from one side wall and from one edge surface a significant distance toward the other side wall and edge surface, said slit being at an oblique angle in longitudinal cross section perpendicular to said side walls so as to create at least two joined parts of said implant portion with respective facing surfaces that are at an angle which differs significantly from a plane perpendicular to said side walls, said joined parts being movable across said slit toward each other, and being slidable along each other such that the two joined parts become laterally displaced with respect to each other.

2. An oral implant as claimed in claim 1 wherein the implant portion further defines vent holes passing through said implant portion at least part of the way from one side wall to the other.

3. An oral implant as claimed in claim 1 wherein the implant portion further includes gripping locations, at least one gripping location being on a respective one of each of said two joined parts of said implant portion and being adapted to facilitate attachment to said parts so as to apply sufficient squeezing force thereto that the parts move toward each other.

4. An oral implant as claimed in claim 3 wherein said gripping locations include at least one recess in the one edge surface of said two joined parts adjacent the slit.

5. An oral implant as claimed in claim 4 wherein said implant portion further includes at least one neck portion extending from said one edge surface, said neck portion being adjacent said slit on the other of said two joined parts, said neck portion acting as part of a mount for the artifical tooth structure and as one of said gripping locations.

6. An oral implant as claimed in claim 1 wherein said implant portion further defines a bending hole at the end of said slit, said bending hole passing from one side wall to the other, whereby the movement of said facing surfaces toward and along each other is facilitated.

7. An oral implant as claimed in claim 6 wherein a joining section of said implant portion connects said two joined parts of said implant portion between the outer edge of said bending hole and the other edge surface, the thickness of said joining section determining the force needed to move said facing surfaces toward and along each other.

8. An oral implant as claimed in claim 1 wherein the implant portion has two of said slits located toward opposite ends thereof and extending from one side wall completely through the implant portion to the other so as to form center, left and right joined parts, wherein movement of said left and right joined parts toward said center part causes said left and right joined parts to move laterally in the same direction with respect to said center part.

9. An oral implant as claimed in claim 8 further including gripping locations in said left and right joined parts, said gripping locations being recesses in said one edge surface adapted to facilitate attachment to said left and right joined parts so as to apply sufficient squeezing force thereto to cause them to move toward the center part.

10. An oral implant as claimed in claim 1 wherein said slit is also oblique in lateral vertical cross section to form a taper shape for said joined parts towards one of said side walls.

11. An oral implant as claimed in claim 10 wherein said at least one slit is two slits extending in opposite directions from the center of said implant portion so as to form left and right parts joined to said implant portion, said left and right parts including gripping locations adopted to permit said left and right parts to be moved against said implant portion such that they are laterally displaced with respect thereto.

12. An oral implant as claimed in claim 1 further including two posts extending from the ends of said one edge surface of said implant portion at an angle directed away from a perpendicular line at the center of said one edge surface, said posts being attached to respective joined parts, and wherein pivoting of said posts towards a right angle with said one edge surface moves said parts toward each other such that said parts become laterally displaced with respect to each other.

13. An oral implant as claimed in claim 12 further including spherical surfaces at the ends of said posts, said spherical surfaces being adapted to receive said artifical tooth structure and to orient it perpendicularly with respect to said one edge surface.

14. An oral implant as claimed in claim 12 wherein a section of said implant portion joins said joined parts, said section having inclined surfaces which urge said parts laterally when moved into contact with said section.

15. An oral implant as claimed in claim 1 wherein said at least one slit is two crossed slits extending through the implant portion from one side wall to the other so as to create two pairs of opposing parts, movement of the parts of one pair toward each other causing the parts of the other pair to move away from each other.

16. An oral implant as claimed in claim 12 wherein said slit is also oblique in lateral cross section so as to form a tapered shape for said joined parts toward one of said side walls.

17. An oral implant as claimed in claim 1 wherein said implant portion further includes
at least one neck portion attached to and extending from said one edge surface;
a cap portion being adapted to receive the artificial tooth structure, said cap portion having a threaded part; and
a collar rotatably secured about said neck portion, said collar having threads over a section thereof adapted to be received on the threads of said cap.

18. An oral implant as claimed in claim 17 wherein the collar has a gripping surface to facilitate rotation thereof.

19. An oral implant as claimed in claim 17 wherein said collar is secured to said neck by a pin passing laterally through the neck, the collar being located between the one edge surface and the pin, and wherein said cap has an internal threaded cavity and said collar has mating external threads, the internal cavity of said cap also being adapted to receive a portion of said neck.

20. An oral implant as claimed in claim 17 wherein said collar has an external threaded section with a transverse slit through a part of the threaded section so as to created divided threaded parts, and wherein the cap has a threaded interior cavity, the collar threads being arranged so that the screwing of the collar into the cap cavity causes the divided threaded parts of the collar to move toward each other and squeeze the collar onto said neck, and the neck to be received in the cavity of the cap.

21. An oral implant as claimed in claim 17 wherein said neck has threads of one orientation at its free end and said collar has internal threads of the same size and orientation, such that said collar can be screwed onto said neck beyond its threads and held there against rotation in the opposite direction, the collar further has external threads, and said cap has a threaded internal cavity, the threads of said cap and the external collar threads being of the same size and orientation, which orientation is opposite that on the end of said neck, and wherein screwing said collar into said cap causes said neck to be received in said cap cavity.

22. An oral implant as claimed in claim 17 wherein said collar has interior threads and said cap has an exterior threaded extension, the threaded extension of said cap having a slit such that said extension is divided into two threaded parts, said cap further having an interior cavity for receiving said neck, the threads of said collar and cap extension being such that screwing the collar onto said cap extension causes the divided threaded parts of said cap extension to move toward each other and squeeze the cap onto said neck.

23. An oral implant as claimed in claim 17 wherein said cap and said collar have opposing surfaces which come together when said collar is threaded to said cap, said opposing surfaces having alternating projections and recesses that interlock when said cap and collar are threaded tightly together.

24. An oral implant for supporting an artificial tooth structure comprises:
an implant portion adapted to be fitted in an exposed opening in a bone of a patient in the vicinity of the occusal plane, said implant portion including two spaced-apart edge surfaces, and two generally parallel and laterally spaced-apart side walls connecting said edge surfaces;
at least one neck portion attached to an extending from one of said edge surfaces;
a cap portion being adapted to receive the artificial tooth structure, said cap portion having a threaded part; and
a collar located about and rotatably secured to an unthreaded part of said neck portion, said collar having threads over a section thereof adapted to be received on the threads of said cap.

25. An oral implant as claimed in claim 24 wherein the collar has a gripping surface to facilitate rotation thereof.

26. An oral implant as claimed in claim 24 wherein said collar is secured to said neck by a pin passing laterally through the neck, the collar being located between the one edge surface and the pin, and wherein said cap has an internal threaded cavity and said collar has mating external threads, the internal cavity of said cap also being adapted to receive a portion of said neck.

27. An oral implant as claimed in claim 24 wherein said neck has threads of one orientation at its free end and said collar has internal threads of the same size and orientation, such that said collar can be screwed onto said neck beyond its threads and held there against rotation in the opposite direction, the collar further has external threads and said cap has a threaded internal cavity, the threads of said cap and the external collar threads being of the same size and orientation, which orientation is opposite that on the end of said neck, and wherein screwing said collar into said cap causes said neck to be received in said cap cavity.

28. An oral implant as claimed in claim 24 wherein said cap and said collar have opposing surfaces which come together when said collar is threaded to said cap, said opposing surfaces having alternating projections and recesses that interlock when said cap and collar are threaded tightly together.

29. An oral implant for supporting an artificial tooth structure comprises:
an implant portion adapted to be fitted in an exposed opening in a bone of a patient in the vicinity of the occusal plane, said implant portion including two spaced-apart edge surfaces, and two generally parallel and laterally spaced-apart side walls connecting said edge surfaces;
at least one neck portion attached to and extending from one of said edge surfaces;

a cap portion being adapted to receive the artificial tooth structure, said cap portion having a threaded interior cavity; and a collar adapted to be rotatably positioned about said neck portion, said collar having an external threaded section with a transverse slit through a part of the threaded section so as to create divided threaded parts, the collar threads being arranged so that the screwing of the collar into the cap cavity causes the divided threaded parts of the collar to move toward each other to squeeze the collar onto said neck, and the neck to be received in the cavity of the cap.

30. An oral implant for supporting an artificial tooth structure comprises:

an implant portion adapted to be fitted in an exposed opening in a bone of a patient in the vicinity of the occusal plane, said implant portion including two spaced-apart edge surfaces, and two generally parallel and laterally spaced-apart side walls connecting said edge surfaces;

at least one neck portion attached to and extending from one of said edge surfaces;

a cap portion being adapted to receive the artificial tooth structure, said cap portion having a threaded extension, the threaded extension of said cap having a slit such that said extension is divided into two threaded parts, said cap further having an interior cavity for receiving said neck; and a collar adapted to be rotatably located about said neck portion, said collar having interior threads, the threads of said collar and cap extension being such that screwing the collar onto said cap extension causes the divided threaded parts of said cap extension to move toward each other and squeeze the cap onto said neck.

* * * * *